United States Patent …

(12) United States Patent
Bornzin et al.

(10) Patent No.: US 8,634,912 B2
(45) Date of Patent: Jan. 21, 2014

(54) DUAL-CHAMBER LEADLESS INTRA-CARDIAC MEDICAL DEVICE WITH INTRA-CARDIAC EXTENSION

(75) Inventors: Gene A. Bornzin, Simi Valley, CA (US); Gabriel A. Mouchawar, Valencia, CA (US); Xiaoyi Min, Thousand Oaks, CA (US); John W. Poore, South Pasadena, CA (US); Edward Karst, South Pasadena, CA (US); Richard Samade, Northridge, CA (US); Zoltan Somogyi, Simi Valley, CA (US); Didier Theret, Porter Ranch, CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

(21) Appl. No.: 13/352,136

(22) Filed: Jan. 17, 2012

(65) Prior Publication Data

US 2013/0116741 A1    May 9, 2013

Related U.S. Application Data

(60) Provisional application No. 61/555,960, filed on Nov. 4, 2011.

(51) Int. Cl.
*A61N 1/362* (2006.01)

(52) U.S. Cl.
USPC ............... 607/9; 607/119; 607/123; 607/124

(58) Field of Classification Search
USPC ...................... 607/9, 119, 123, 124
See application file for complete search history.

(56) References Cited

U.S. PATENT DOCUMENTS

| | | |
|---|---|---|
| 3,835,864 A | 9/1974 | Rasor et al. |
| 3,835,869 A | 9/1974 | Newman et al. |
| 3,943,936 A | 3/1976 | Rasor et al. |
| 4,987,897 A | 1/1991 | Funke |
| 5,193,540 A | 3/1993 | Schulman et al. |
| 5,358,514 A | 10/1994 | Schulman et al. |
| 5,405,367 A | 4/1995 | Schulman et al. |
| 5,411,535 A | 5/1995 | Fujii et al. |

(Continued)

FOREIGN PATENT DOCUMENTS

| | | |
|---|---|---|
| EP | 1844812 A1 | 10/2007 |
| WO | 2005092431 A1 | 10/2005 |

(Continued)

OTHER PUBLICATIONS

Asirvatham, Samuel J. MD et al., "Intramyocardial Pacing and Sensing for the Enhancement of Cardiac Stimulation and Sensing Specificity," PACE. 2007;30:748-754.

(Continued)

*Primary Examiner* — Joseph Dietrich

(57) ABSTRACT

A leadless intra-cardiac medical device includes a housing that is configured to be implanted entirely within a single local chamber of the heart. A first electrode is provided on the housing at a first position such that when the housing is implanted in the local chamber, the first electrode engages the local wall tissue at a local activation site within the conduction network of the local chamber. An intra-cardiac extension is coupled to the housing and configured to extend from the local chamber into an adjacent chamber of the heart. A stabilization arm of the intra-cardiac extension engages the adjacent chamber. A second electrode on the intra-cardiac extension engages distal wall tissue at a distal activation site within the conduction network of the adjacent chamber.

24 Claims, 8 Drawing Sheets

(56) References Cited

U.S. PATENT DOCUMENTS

| | | | |
|---|---|---|---|
| 5,487,758 | A | 1/1996 | Hoegnelid et al. |
| 5,545,201 | A | 8/1996 | Helland et al. |
| 5,679,022 | A | 10/1997 | Cappa et al. |
| 5,814,089 | A | 9/1998 | Stokes et al. |
| 6,141,588 | A | 10/2000 | Cox et al. |
| 6,164,284 | A | 12/2000 | Schulman et al. |
| 6,181,965 | B1 | 1/2001 | Loeb et al. |
| 6,185,452 | B1 | 2/2001 | Schulman et al. |
| 6,208,894 | B1 | 3/2001 | Schulman et al. |
| 6,434,428 | B1 | 8/2002 | Sloman et al. |
| 6,754,536 | B2 | 6/2004 | Swoyer et al. |
| 7,047,076 | B1 | 5/2006 | Li et al. |
| 7,082,336 | B2 | 7/2006 | Ransbury et al. |
| 7,114,502 | B2 | 10/2006 | Schulman et al. |
| 7,363,087 | B2 | 4/2008 | Nghiem et al. |
| 7,383,091 | B1 | 6/2008 | Chitre et al. |
| 7,513,257 | B2 | 4/2009 | Schulman et al. |
| 7,565,195 | B1 | 7/2009 | Kroll et al. |
| 7,634,313 | B1 | 12/2009 | Kroll et al. |
| 7,643,872 | B2 | 1/2010 | Min et al. |
| 7,801,626 | B2 | 9/2010 | Moser |
| 7,860,570 | B2 | 12/2010 | Whitehurst et al. |
| 7,894,915 | B1 | 2/2011 | Chitre et al. |
| 7,899,555 | B2 | 3/2011 | Morgan et al. |
| 7,937,148 | B2 | 5/2011 | Jacobson |
| 7,945,333 | B2 | 5/2011 | Jacobson |
| 8,010,209 | B2 | 8/2011 | Jacobson |
| 8,032,219 | B2 | 10/2011 | Neumann et al. |
| 2004/0015204 | A1 | 1/2004 | Whitehurst et al. |
| 2004/0015205 | A1 | 1/2004 | Whitehurst et al. |
| 2004/0147973 | A1 | 7/2004 | Hauser |
| 2006/0009831 | A1 | 1/2006 | Lau et al. |
| 2006/0135999 | A1 | 6/2006 | Bodner et al. |
| 2007/0055310 | A1 | 3/2007 | Lau |
| 2007/0088396 | A1 | 4/2007 | Jacobson |
| 2007/0088400 | A1 | 4/2007 | Jacobson |
| 2008/0097566 | A1 | 4/2008 | Colliou |
| 2008/0255647 | A1 | 10/2008 | Jensen et al. |
| 2009/0082828 | A1 | 3/2009 | Ostroff |
| 2009/0299433 | A1 | 12/2009 | Dingman et al. |
| 2010/0010381 | A1 | 1/2010 | Skelton et al. |
| 2010/0198288 | A1 | 8/2010 | Ostroff |
| 2011/0071586 | A1 | 3/2011 | Jacobson |
| 2011/0077708 | A1 | 3/2011 | Ostroff |
| 2011/0208260 | A1 | 8/2011 | Jacobson |
| 2011/0218587 | A1 | 9/2011 | Jacobson |
| 2011/0238077 | A1 | 9/2011 | Wenger |
| 2011/0251660 | A1 | 10/2011 | Griswold |
| 2011/0251662 | A1 | 10/2011 | Griswold et al. |

FOREIGN PATENT DOCUMENTS

| | | | |
|---|---|---|---|
| WO | 2007047681 | A2 | 4/2007 |
| WO | 2007047681 | A3 | 9/2008 |
| WO | 2009039400 | A1 | 3/2009 |
| WO | 2009078751 | A1 | 6/2009 |
| WO | 2010088687 | A1 | 8/2010 |

OTHER PUBLICATIONS

Brinker, Jeffrey A., "Endocardial Pacing Leads: The Good, the Bad, and the Ugly," PACE. 1995;18(Pt 1):953-954.

Calvagna, Giuseppe M. et al., "A complication of pacemaker lead extraction: pulmonary embolization of an electrode fragment," Europace. 2010;12:613.

Da Costa, Sergio Sidney Do Carmo et al., "Incidence and Risk Factors of Upper Extremity Deep Vein Lesions After Permanent Transvenous Pacemaker Implant: A 6-Month Follow-up Prospective Study," PACE. 2002;25:1301-1306.

Hauser, Robert G. et al., "Deaths and cardiovascular injuries due to device-assisted implantable cardioverter-defibrillator and pacemaker lead extraction," Europace. 2010;12:395-401.

Heaven, D.J. et al., "Pacemaker lead related tricuspid stenosis: a report of two cases," Heart. 2000;83:351-352.

Henz, Benhur D. MD et al., "Synchronous Ventricular Pacing without Crossing thetricuspid Valve or Entering the Coronary Sinus—Preliminary Results," J Cardiovasc Electrophysiol. (Dec. 2009);20:1391-1397.

Hesselson, Aaron B. Bsee et al., "Deleterious Effects of Long-Term Single-chamber Ventricular Pacing in Patients With Sick Sinus Syndrome: The Hidden Benefits of dual-Chamber Pacing," J Am Coll Cardiol. 1992;19:1542-1549.

Klug, Didier MD et al., "Systemic Infection Related to Endocardities on Pacemaker Leads—Clinical Presentation and Management," Circulation. 1997;95:2098-2107.

Korkeila, Petri et al., "Clinical and laboratory risk factors of thrombotic complications after pacemaker implantation: a prospective study," Europace. 2010;12:817-824.

Marrie, Thomas J. MD et al., "A Scanning and Transmission Electron Microscopic Study of an Infected Endocardial Pacmaker Lead," Circulation. 1982;66(6):1339-1341.

Menozzi, Carlo et al., "Intrapatient Comparison Between Chronic VVIR and DDD pacing in Patients Affected by High Degree AV Block Without Heart Failure," PACE. (Dec. 1990—Pt II);13:1816-1822.

Stellbrink, Christoph et al.,"Technical considerations in implanting left ventricular pacing leads for cardiac resynchronization therapy," European Heart Journal Supplements. 2004;6(Supp D):D43-D46.

Stickler, J. William PhD, "Totally Self-Contained Intracardiac Pacemaker," J Electrocardiology. 1970;3(3-4):325-331.

Van Rooden, Cornelis J. MD et al., "Incidence and Risk Factors of Early Venous Thrombosis Associated with Permanent Pacemaker Leads," J Cardiovasc Electrophysiol. (Nov. 2004);15:1258-1262.

Vardas, P.E. et al., "A Miniature Pacemaker Introduced Intravenously and Implanted Endocardially. Preliminary Findings from an Experimental Study," Eur J Card Pacing Electrophysiol. 1991;1:27-30.

Voet, J.G. et al., "Pacemaker lead infection: report of three cases and review of the literature," Heart. 1999;81:88-91.

Walters, M.I. et al., "Pulmonary Embolization of a Pacing Electrode Fragment Complicating Lead Extraction," PACE. 1999;22:823-824.

DUAL-CHAMBER LEADLESS INTRA-CARDIAC MEDICAL DEVICE WITH INTRA-CARDIAC EXTENSION

CROSS REFERENCE TO RELATED APPLICATIONS

This application relates to and claims priority benefits from U.S. Provisional Application No. 61/555,960, filed Nov. 4, 2011, entitled "Implantable Medical Device and Intra-Cardiac Lead with Stabilizer Extension," which is hereby incorporated by reference in its entirety. This application also relates to U.S. patent application Ser. Nos.: 13/352,048, filed Jan. 17, 2012, entitled "Single-Chamber Leadless Intra-Cardiac Medical Device with Dual-Chamber Functionality," and 13/352,101, filed Jan. 17, 2012 entitled "Single-Chamber Leadless Intra-Cardiac Medical Device with Dual Chamber Functionality and Shaped Stabilization Intra-Cardiac Extension," which are hereby incorporated by reference in their entirety.

FIELD OF THE INVENTION

Embodiments of the present invention generally relate to implantable medical devices, and more particularly to leadless intra-cardiac medical devices that include an intra-cardiac extension that affords dual chamber functionality and device stabilization. As used herein, the term "leadless" generally refers to an absence of electrically-conductive leads that traverse vessels outside of the intra-cardiac space, while "intra-cardiac" means generally, entirely within the heart and associated vessels, such as the SVC, IVC, CS, pulmonary arteries and the like.

BACKGROUND OF THE INVENTION

Current implantable medical devices for cardiac applications, such as pacemakers, include a "housing" or "can" and one or more electrically-conductive leads that connect to the can through an electro-mechanical connection. The can is implanted outside of the heart, in the pectoral region of a patient and contains electronics (e.g., a power source, microprocessor, capacitors, etc.) that provide pacemaker functionality. The leads traverse blood vessels between the can and heart chambers in order to position one or more electrodes carried by the leads within the heart, thereby allowing the device electronics to electrically excite or pace cardiac tissue and measure or sense myocardial electrical activity.

To sense atrial cardiac signals and to provide right atrial chamber stimulation therapy, the can is coupled to an implantable right atrial lead including at least one atrial tip electrode that typically is implanted in the patient's right atrial appendage. The right atrial lead may also include an atrial ring electrode to allow bipolar stimulation or sensing in combination with the atrial tip electrode.

Before implantation of the can into a subcutaneous pocket of the patient, however, an external pacing and measuring device known as a pacing system analyzer (PSA) is used to ensure adequate lead placement, maintain basic cardiac functions, and evaluate pacing parameters for an initial programming of the device. In other words, a PSA is a system analyzer that is used to test an implantable device, such as an implantable pacemaker.

To sense the left atrial and left ventricular cardiac signals and to provide left-chamber stimulation therapy, the can is coupled to the "coronary sinus" lead designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead is designed to: receive atrial and/or ventricular cardiac signals; deliver left ventricular pacing therapy using at least one left ventricular tip electrode for unipolar configurations or in combination with left ventricular ring electrode for bipolar configurations; deliver left atrial pacing therapy using at least one left atrial ring electrode as well as shocking therapy using at least one left atrial coil electrode.

To sense right atrial and right ventricular cardiac signals and to provide right-chamber stimulation therapy, the can is coupled to an implantable right ventricular lead including a right ventricular (RV) tip electrode, a right ventricular ring electrode, a right ventricular coil electrode, a superior vena cava (SVC) coil electrode, and so on. Typically, the right ventricular lead is inserted transvenously into the heart so as to place the right ventricular tip electrode in the right ventricular apex such that the RV coil electrode is positioned in the right ventricle and the SVC coil electrode will be positioned in the right atrium and/or superior vena cava. Accordingly, the right ventricular lead is capable of receiving cardiac signals, and delivering stimulation in the form of pacing and shock therapy to the right ventricle.

Although a portion of the leads are located within the heart, a substantial portion of the leads, as well as the can itself are outside of the patient's heart. Consequently, bacteria and the like may be introduced into the patient's heart through the leads, as well as the can, thereby increasing the risk of infection within the heart. Additionally, because the can is outside of the heart, the patient may be susceptible to Twiddler's syndrome, which is a condition caused by the shape and weight of the can itself. Twiddler's syndrome is typically characterized by a subconscious, inadvertent, or deliberate rotation of the can within the subcutaneous pocket formed in the patient. In one example, a lead may retract and begin to wrap around the can. Also, leads may dislodge from the endocardium and cause the device to malfunction. Further, in another typical symptom of Twiddler's syndrome, the device may stimulate the diaphragm, vagus, or phrenic nerve, pectoral muscles, or brachial plexus. Overall, Twiddler's syndrome may result in sudden cardiac arrest due to conduction disturbances related to the device.

In addition to the foregoing complications, implanted leads may experience certain further complications, such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction.

To combat the foregoing limitations and complications, small sized devices configured for intra-cardiac implant have been proposed. These devices, termed leadless pacemakers (LLPM) are typically characterized by the following features: they are devoid of leads that pass out of the heart to another component, such as a pacemaker can outside of the heart; they include electrodes that are affixed directly to the can of the device; the entire device is attached to the heart; and the device is capable of pacing and sensing in the chamber of the heart where it is implanted.

LLPM devices that have been proposed thus far offer limited functional capability. These LLPM devices are able to sense in one chamber and deliver pacing pulses in that same chamber, and thus offer single chamber functionality. For example, an LLPM device that is located in the right atrium would be limited to offering AAI mode functionality. An AAI mode LLPM can only sense in the right atrium, pace in the right atrium and inhibit pacing function when an intrinsic event is detected in the right atrium within a preset time limit. Similarly, an LLPM device that is located in the right ventricle would be limited to offering VVI mode functionality. A VVI mode LLPM can only sense in the right ventricle, pace in the right ventricle and inhibit pacing function when an intrinsic event is detected in the right ventricle within a preset time limit. To gain widespread acceptance by clinicians, it would be highly desired for LLPM devices to have dual chamber pacing/sensing capability (DDD mode) along with other features, such as rate adaptive pacing.

It has been proposed to implant sets of multiple LLPM devices within a single patient, such as one or more LLPM devices located in the right atrium and one or more LLPM devices located in the right ventricle. The atrial LLPM devices and the ventricular LLPM devices wirelessly communicate with one another to convey pacing and sensing information therebetween to coordinate pacing and sensing operations between the various LLPM devices.

However, these sets of multiple LLPM devices experience various limitations. For example, each of the LLPM devices must expend significant power to maintain the wireless communications links. The wireless communications links should be maintained continuously in order to constantly convey pacing and sensing information between, for example, atrial LLPM device(s) and ventricular LLPM device(s). This pacing and sensing information is necessary to maintain continuous synchronous operation, which in turn draws a large amount of battery power.

Further, it is difficult to maintain a reliable wireless communications link between LLPM devices. The LLPM devices utilize low power transceivers that are located in a constantly changing environment within the associated heart chamber. The transmission characteristics of the environment surrounding the LLPM device change due in part to the continuous cyclical motion of the heart and change in blood volume. Hence, the potential exists that the communications link is broken or intermittent.

SUMMARY OF THE INVENTION

In accordance with embodiments herein, a leadless intra-cardiac medical device (LIMD) comprises a housing configured to be implanted entirely within a single local chamber of the heart. A base is provided on the housing, where the base is configured to be secured to the local chamber. A first electrode is provided on the housing at a first position such that when the housing is implanted in the local chamber, the first electrode engages the local wall tissue at a local activation site within the conduction network of the local chamber. The LIMD also includes an intra-cardiac extension having a proximal end, a distal end and an extension body extending there between. The proximal end is coupled to the housing and is located in the local chamber. The extension body extends between the proximal and distal ends. The extension body includes a stabilization arm provided at the distal end thereof. The extension body is sufficient in length to extend from the local chamber into an adjacent chamber of the heart. The stabilizer end-segment is located at the distal end and extends in a first lateral direction to engage a first region of the heart. The active interim-segment is located at an intermediate point along the extension body between the stabilization extension and the proximal end. The active interim-segment extends in a second lateral direction to engage a second region of wall tissue of the adjacent chamber. A second electrode is provided within the active interim-segment of the extension body. The second electrode engages distal wall tissue at a distal activation site within the conduction network of the adjacent chamber. A controller is provided within the housing to cause stimulus pulses to be delivered, in a dual chamber synchronous manner, through the first and second electrodes to the local and distal activation sites, respectively.

In accordance with embodiments herein, the extension body further comprises an active interim-segment, provided at an intermediate point along the extension body, and a third electrode. The second and third electrodes are located within the active interim-segment. The second and third electrodes are being electrically separated from one another and configured to operate in at least one of a bipolar sensing and bipolar pacing mode. In accordance with embodiments herein, the extension body further comprises an active interim-segment, wherein the active interim-segment is pre-formed in a curved shape and includes the second electrode and a third electrode located on the extension body in a trough of the curved shape in the active interim-segment, the curved shape configured to following a contour of an interior of a right atrial appendage.

In accordance with embodiments herein, the first and second regions represent a superior vena cava and a right atrial appendage of the right atrium, respectively. Optionally, the controller is configured to time delivery of the stimulus pulses at the distal activation site to cause contraction of the adjacent chamber in a predetermined relation to contraction of the local chamber. Optionally, the extension body further comprises an active interim-segment and a chamber transition sub-segment that extends from the proximal end to the active interim-segment, the chamber transition sub-segment being sufficient in length to locate the active interim-segment in a right atrial appendage. The controller may be configured to control delivery of the stimulus pulses from the first and second electrodes in accordance with a DDD pacing mode to a right atrium and right ventricle, while the housing is entirely located in one of the right atrium and right ventricle. Optionally, the controller is configured to control delivery of the stimulus pulses from the first and second electrodes in accordance with a DDD pacing mode to a left atrium and left ventricle, while the housing is entirely located in one of the left atrium and left ventricle.

Optionally, the stabilization arm includes a flexible stabilization end-segment wrapped into at least one turn having a pre-formed diameter. The extension body further may further comprises an active interim-segment located between the stabilization arm and the proximal end, the active interim-segment and the stabilization arm extend into and engage opposed areas of the local wall tissue of the local chamber.

In accordance with embodiments herein, methods are described for implanting a leadless intra-cardiac medical device (LIMD). The IMD includes a housing with a base, a first electrode provided on the housing, an intra-cardiac extension having a proximal end, a distal end and an extension body extending there between. The proximal end is coupled to the housing, the extension body includes a stabilization extension provided at the distal end of the intra-cardiac extension, and an active interim-segment located at an intermediate point along the extension body between the stabilization extension and the proximal end of the intra-cardiac extension, a second electrode is provided on the active interim-segment. The method includes guiding the housing, utilizing an introducer, to a local activation site within a conductive network of the local chamber; positioning the first electrode to engage wall tissue at the local activation site within the conductive network of the local chamber; and actively securing the housing to tissue of interest at the local activation site. The method also includes guiding the active interim-segment, utilizing the introducer, to a distal activation site within a conductive network of an adjacent chamber; positioning the second electrode to engage tissue of interest at the distal activation site within the conductive network of the adjacent chamber; and configuring a controller within the housing to cause stimulus pulses to be delivered, in a dual chamber synchronous manner, through the first electrode to the local activation site, and through the second electrode to the distal activation site.

Optionally, the active interim-segment of the LIMD may include a third electrode electrically separated from the second electrode; in which case the method may further include configuring the controller to operate in at least one of a bipolar sensing mode and a bipolar pacing mode using the second and third electrodes.

Optionally, the method may further include loading the LIMD into a sheath of the introducer such that a memorized, pre-formed shape of the intra-cardiac extension is changed to a temporary, extended or dilated introducer state; and after actively securing the housing to the tissue of interest, at least partially retracting the introducer such that, as the intra-cardiac extension is discharged from a distal end of the sheath, thereby allowing the intra-cardiac extension to return to the memorized, pre-formed shape. Optionally, actively securing the housing may comprise applying rotational force to the stabilization extension which causes an active fixation member on the housing to become securely affixed to the wall tissue.

Optionally, the method may also include, when the active interim-segment exits from the introducer, permitting the active interim-segment to bend into a curved shape sufficient to extend into and engage a contour of an interior of the heart or vessel. The method may also include guiding the stabilization extension to engage a first region of the heart, the first region representing at least one of a superior vena cava, an inferior vena cava, a coronary sinus, and a pulmonary artery. In this case, the stabilization extension may include a stabilizer end-segment that is pre-formed to wrap into at least one turn that is predisposed to radially expand to a diameter sufficient to fit against an interior of at least one of a superior vena cava, an inferior vena cava, a coronary sinus, and a pulmonary artery.

Optionally, the method may also include configuring the controller to control delivery of the stimulus pulses from the first and second electrodes in accordance with a DDD pacing mode to a right atrium and right ventricle, while the housing is entirely located in the right side of the heart. Optionally, the method may also include configuring the controller to control delivery of the stimulus pulses from the first and second electrodes in accordance with a DDD pacing mode to a left atrium and left ventricle, while the housing is entirely located in the left side of the heart.

DETAILED DESCRIPTION

Dual-chamber PPMs, operating in the DDD mode, are indicated for patients with complete atrioventricular (AV) block, sick sinus syndrome, and paroxysmal AV block. The use of DDD mode PPMs in patients with a high degree of AV block is shown to improve subjective metrics of patient life and increase peak velocity and cardiac output, compared to VVIR PPMs. Additionally, another study demonstrates reduced incidence of atrial fibrillation (AF) and increased patient longevity in patients with sick sinus syndrome after the time of DDD PPM implant. These benefits, accrued to the three previously-described subgroups of implant patients, provide a strong impetus for using DDD PPMs in those recipients.

Figure 1A:
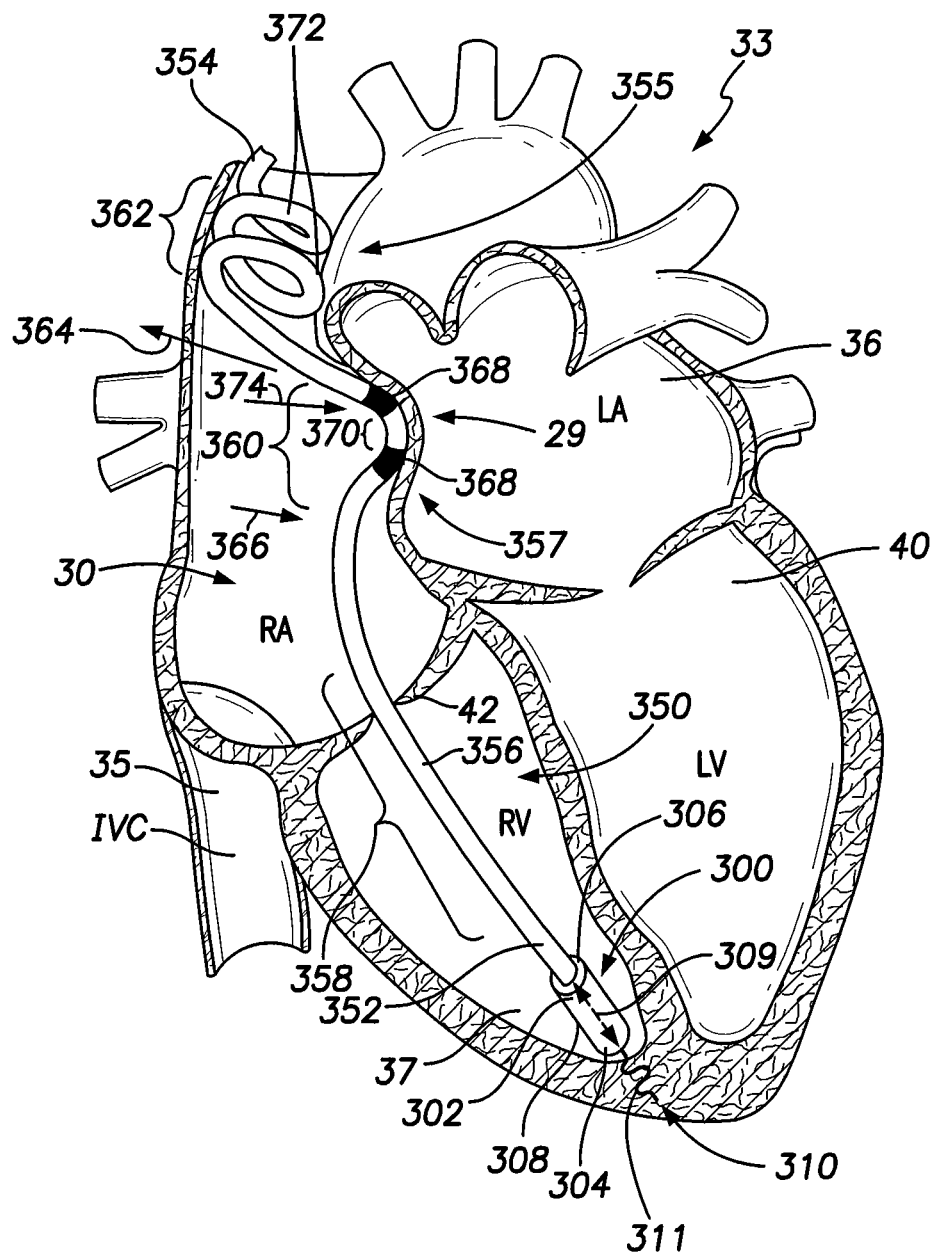
FIG. 1A provides a sectional view of the patient's heart and shows a leadless intra-cardiac medical device (LIMD) having housing and an intra-cardiac extension, and implanted in the right side of the heart.

FIG. 1A provides a sectional view of the patient's heart 33 and shows a leadless intra-cardiac medical device (LIMD) 300. The LIMD 300 has been placed through the superior vena cava, through the right atrium 30 and into the right ventricle 37 of the heart 33. Optionally, the LIMD 300 may have been introduced through the inferior vena cava 35. As another option, the LIMD 300 may be introduced into the left atrium through a pulmonary vein, into the left ventricle through the intraventricular septum, into the left ventricle through a vein, and the like. The atrial septum divides the two atria 30, 36, while the tricuspid valve 42 is shown between the right atrium 30 and right ventricle 37. FIG. 1A also illustrates the right atrial appendage 29. The reader will appreciate that the view of FIG. 1A is simplified and somewhat schematic, but that nevertheless FIG. 1A and the other views included herein will suffice to illustrate adequately the placement and operation of certain embodiments. The term "septum" shall be used throughout to generally refer to any portion of the heart separating two chambers (e.g. RA to LA, RA to RV, RV to LV, LA to LV, RA to LV).

The LIMD 300 is formed in accordance with an embodiment and may represent a pacemaker that functions in a DDD-mode, a cardiac resynchronization device, a cardioverter, a defibrillator and the like. When in DDD-mode, the LIMD 300 may sense in two chambers, pace in two chambers and inhibit pacing in either chamber based on intrinsic events sensed in that chamber or in the other chamber. The LIMD 300 is configured to be implanted entirely within a single side of the heart. For example, the LIMD 300 may be implanted entirely and solely within the right side of the heart and extend into and between the right atrium and the right ventricle. Optionally, the LIMD 300 may be implanted entirely and solely within the left side of the heart and extend into and between the left atrium or left ventricle through more invasive implant methods. As described further below, the LIMD 300 includes a housing and an intra-cardiac extension that extends from the module. The LIMD is configured such that the housing may be located in one chamber, such as a right ventricle, while the extension extends into an adjacent chamber, such as the right atrium.

For convenience, hereafter the chamber in which the LIMD 300 housing is implanted shall be referred to as the "local" chamber. The local chamber includes a local chamber wall that is physiologically response to local activation events originating in the local chamber. The local chamber is at least partially surrounded by local wall tissue that forms or constitutes at least part of a conduction network for the associated chamber. For example, during normal operation, the wall tissue of the right atrium contracts in response to an intrinsic local activation event that originates at the sinoatrial (SA) node and in response to conduction that propagates along the atrial wall tissue. For example, tissue of the right atrium chamber wall in a healthy heart follows a conduction pattern, through depolarization, that originates at the SA node and moves downward about the right atrium until reaching the atria ventricular (AV) node. The conduction pattern moves along the chamber wall as the right atrium wall contracts.

The term "adjacent" chamber shall refer to any chamber separated from the local chamber by tissue (e.g., the RV, LV and LA are adjacent chambers to the RA; the RA and LV are adjacent chambers to the LA; the RA and RV are adjacent to one another; the RV and LV are adjacent to one another, and the LV and LA are adjacent to one another).

As briefly described above, the LIMD 300 includes a housing 302 that includes a base 304 and a top end 306. The housing 302 extends along a longitudinal axis 309 between the base 304 and the top end 306. The housing 302 is elongated and tubular in shape and extends along the longitudinal axis 309. The base 304 is configured to be secured to the local chamber. In the example of FIG. 1A, the base 304 is secured to the right ventricle 37. Optionally, the LIMD 300 may be located in, and the base 304 secured to the wall of the left ventricle 40, left atrium 36 or right atrium 30.

The base 304 includes an active fixation member 310 provided thereon and extending outward from the base 304 in a direction generally along the longitudinal axis 309. A first electrode 311 (also referred to as an active electrode area) is provided on the active fixation member 310. The electrode 311 is provided at a first position such that, when the housing 302 is implanted in the local chamber, the first electrode 311 engages the local wall tissue at a local activation site within the conduction network of the local chamber (e.g., within the ventricular wall tissue at the apex of the right ventricle).

An intra-cardiac (IC) extension 350 has a proximal end 352, a distal end 354 and a extension body 356 extending there between. The term "intra-cardiac" is used to indicate that the extension 350 "generally" remains within the heart and associated vessels, such as the SVC, IVC, CS, pulmonary arteries and the like. LIMD 300 The proximal end 352 is permanently or removably (through a header style connector) coupled to the housing 302 and located in the local chamber. A stabilization arm, generally denoted at 355, is provided on the distal end 352 of the extension body 356. A right atrial appendage (RAA) fixation mechanism, generally denoted at 357, is provided at an intermediate point along the length of the extension body 356 and aligned with the RAA 29.

In the example of FIG. 1A, the extension body 356 including a chamber transition sub-segment 358, an active interim-segment 360 and a stabilizer end-segment 362. The stabilization end-segment 362 is one exemplary structural implementation of the stabilization arm 355. The RAA fixation mechanism 357 is one exemplary structural implementation of an active interim-segment 360. The chamber transition sub-segment 358 is sufficient in length to extend from the local chamber (e.g., the right ventricle) through the tricuspid valve into an adjacent chamber (e.g., the right atrium). The chamber transition sub-segment 358 extends upward out of the right ventricle in a direction that generally follows the longitudinal axis 309.

The extension body 356 is formed of a biocompatible insulated material such as EFTE, silicon, OPTIM and the like. Internal structures of the exemplary embodiments of the extension body 356 are discussed below. In general, the extension body 356 is formed of materials that are flexible yet exhibit a desired degree of shape memory such that once implanted, the active interim-segment 360 and stabilizer end-segment 362 are biased to return to a pre-formed shape. One or more insulated conductive wires are held within the extension body 356 and span from the housing 302 to any sensors or electrodes provided on the extension body 356.

The stabilizer end-segment 362 is located at the distal end 354 and in a pre-formed shape that is biased to extend slightly outward in a lateral direction (generally denoted at 364) relative to a length of the chamber in which the stabilizer end-segment 362 is located. The stabilizer end-segment 362 engages a first region of the heart. For example, the stabilizer end-segment 362 may extend upward into and engage the SVC. Optionally, the stabilizer end-segment 362 may extend downward into and engage the IVC 35. Optionally, the stabilizer end segment 362 may extend into the coronary sinus, pulmonary artery and the like.

The stabilizer end-segment 362 is pre-formed into a pre-determined shape based upon which portion of the chamber is to be engaged. The flexible stabilizer end-segment 362 may be wrapped into at least one turn 372 having a pre-formed diameter. For example, when intended to securely engage the SVC, the stabilizer end-segment 362 may be formed into a spiral shape with one or more windings or turns 372 that are pre-disposed or biased to radially expand to a diameter sufficient to firmly fit against the interior walls of the SVC. When intended to securely engage the IVC, the stabilizer end-segment 362 may be formed with turns 372 that radially expand to a different diameter sufficient to firmly fit against the interior walls of the IVC.

Optionally, the stabilizer end-segment 362 may utilize alternative shapes for SVC stabilization, such as an S-shape, a T-shape, a Y-shape, a U-shape and the like. Optionally, the stabilizer end-segment 362 may be split into multiple (e.g., 2-4) stabilizer end-segments that project outward in different directions and contact different areas of the wall tissue. A conductor wire extends within the extension body 356 from the housing 302 to a second electrode 368, and the conductor terminates at the second electrode such that the stabilizer end segment 362 is void of electrodes and conductor wires. When the stabilizer end-segment 362 lacks any sensors or electrodes, the end-segment 362 will also lack any internal conductive wires.

Optionally, the stabilizer end-segment 362 may include one or more conductors, spanning from the distal end 354 to the housing 302, to be coupled to a PSA or programmer during implantation to provide communications, power, remote access to electrodes and the like.

The active interim-segment 360 is biased, by the stabilizer end-segment 362, to extend in a second transverse direction 366 away from the direction 364 and toward the septum or atrial appendage. The active interim-segment 360 has a pre-formed curved shape, such as a large C-shape, or U-shape. The active interim-segment 360 includes one or more electrodes 368 that are provided thereon and in a trough area 374 of the C-shape or U-shape. The electrodes 368 are spaced apart from one another, within the trough area 374, by an inter-electrode spacing 370. The trough area 374 of the active interim-segment 360, and thus the electrodes 368, are biased in the transverse appendage or septal direction 366 to engage a second region of wall tissue of the adjacent chamber in which the active interim-segment 360 is located. For example, the second electrodes 368 may be biased to engage wall tissue in the right atrial appendage 29. The second electrodes 368 engage distal wall tissue at a distal activation site (relative to the chamber which the LIMD 300 is implanted) within the conduction network of the adjacent chamber. Optionally, tines or other active fixation members may be included around the hump or trough portion of the active interim-segment 360 in order to improve fixation as the RAA fixation mechanism.

The extension body 356 is comprised of a flexible material having a pre-formed, memorized, permanent implanted state that is shaped to conform to select anatomical contours in the heart and to bias the active interim-segment 360 and stabilization arm 355 against the wall tissue at regions of interest. In an embodiment, the curved shape may be configured to follow a contour of an interior of a right atrial appendage. One curved shape may be used for all patients. As another example, prior to implant, the patient's heart may be analyzed to identify the size of one or more chambers of interest and to identify the size and/or shape of the right atrial appendage. In this example, different intra-cardiac extensions 350 may be available with different size and/or shape active interim-segments 360. The physician may select the intra-cardiac extension 350 that represents the closest match to the size/shape of the patient's chamber in which the intra-cardiac extension 350 is to be implanted.

Electronics, including pulse generators and a microcontroller are provided within the housing 302. The electronics may be configured to cause stimulus pulses to be delivered, in a dual chamber synchronous manner, through anode/cathode electrode pairs formed from available includes selected from one or more first electrodes 311, one or more second electrodes 368 and a housing electrode 312 (shown in FIG. 2). For example, two first electrodes 311 or a first electrode 311 and a housing electrode 312 may from an electrode pair at the local activation site, while two second electrodes 368 may form an electrode at the distal activation site. The stimulus pulses delivered at the distal activation site are timed to cause contraction of the adjacent chamber in a predetermined relation to contraction of the local chamber. For example, the LIMD 300 may be configured to control delivery of the stimulus pulses from the first electrode 311/housing electrode 312 and the second electrodes 368 in accordance with a DDD pacing mode to a right atrium and right ventricle, while the housing 302 is entirely located in one of the right atrium and right ventricle and the LIMD 300 itself is located entirely within the right side of the heart. Alternatively, the controller may be configured to control delivery of the stimulus pulses from the first electrode 311/housing electrode and the second electrodes 368 in accordance with a DDD pacing mode to a left atrium and left ventricle, while the housing 302 is entirely located in one of the left atrium and left ventricle and the LIMD 300 itself is located entirely within the left side of the heart.

The base 304 may include multiple electrodes 311 securely affixed thereto and projected outward. For example, the electrodes 311 may be formed as large semi-circular spikes or large gauge wires. A pair of electrodes 311 may be located on opposite sides of, and wound in a common direction with, an inner electrode (not shown). The electrodes 311 are provided directly on the housing 302 of the LIMD 300 at a first position, namely at or proximate to a periphery of the base 304 of the housing 302.

The electrodes 311, 368 may be electrically configured to operate as multiple cathode electrodes that are actively fixated or passively held against the wall tissue at tissue of interest. The electrode 311 may be configured as a screw with a large pitch (e.g. length between adjacent turns), large diameter and may have a length that is relatively short. Optionally, the electrode 311 may be a screw with a small pitch, small diameter and longer length. The screw shape of the electrode 311 is used to firmly adhere to the wall tissue. The electrode 311 may have very little or no insulation material thereon to facilitate a good electrical connection to local wall tissue along the majority or the entire length of the electrode 311 for delivering stimulus pulses and sensing electrical activity in the local chamber where the housing 302 is located.

Figure 1B:
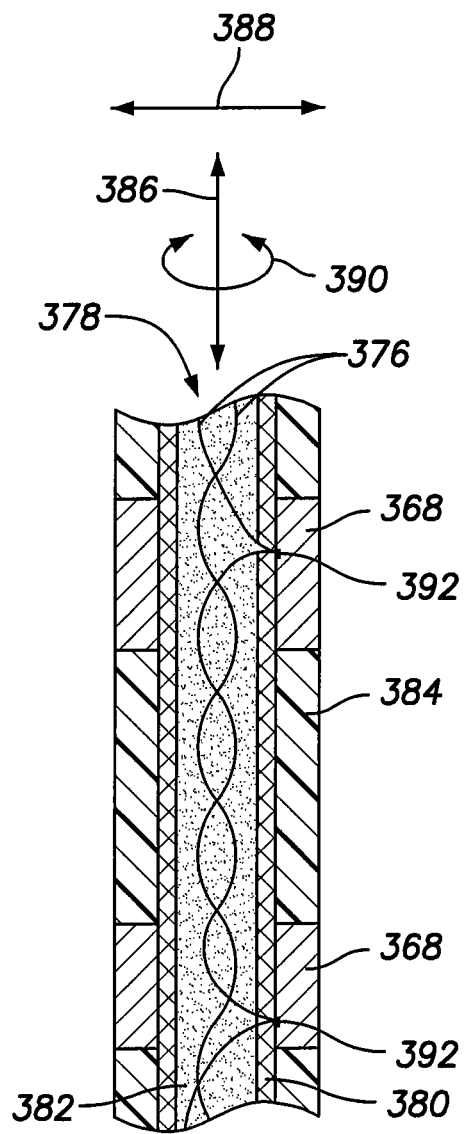
FIG. 1B illustrates a cross section of the active interim-segment from the intra-cardiac extension of FIG. 1A

FIG. 1B illustrates a cross section of the active interim-segment 360 from the intra-cardiac extension 350 of FIG. 1A. The active interim-segment 360 includes one or more insulated conductors 376 that are connected to corresponding electrodes 368. The conductors 376 are connected through a switch to electronics within the housing 302 to perform sensing and/or deliver stimulus pulses. The conductors 376 may be wound about one another in a helical manner. The conductors 376 extend along a core 378 and the conductors 376 are radially surrounded by an elongated braid 380. The braid 380 may be made of steel or wire mesh, or have a honeycomb pattern that resists compression or extension along the length of the extension body (as denoted by longitudinal direction 386). The braid 380 is flexible in a lateral direction 388 in order to be bent side to side during implant and following implant. The mesh or honeycomb configuration of the braid 380 affords strong resistance to torque about the length of the extension body 356 when turned in the rotational direction 390 about the longitudinal direction 386. It is desirable to be resistant to torque in order that, during implant, when a rotational force is applied to one end of the extension body 356, substantially all of such rotational force is conveyed along the length of the extension body 356 to the opposite end. As explained hereafter, the braid 380 facilitates delivery of rotational forces and longitudinal pressure to the LIMD 300 and the active fixation member 310 during implant.

Optionally, the extension body 356 may further includes an insulation material 382 provided around the conductors 376 and around the braid 380. An insulated, flexible, biocompatible shell 384 is formed over the braid 380. The electrodes 368 are connected to separate corresponding conductors 376 at contacts 392. The electrodes 368 may be formed as ring electrodes, coil electrodes, pin or bump electrodes and the like. While two electrodes 368 are illustrated it is understood that only one or more than two electrodes 368 may be provided on the extension body 356. The electrodes 368 may be provided at various points about the perimeter of the extension body 356 and at multiple points along the length of the extension body 356.

The electrodes 368 are separated from the braid 380 by insulation (e.g. part of the shell 384). The electrodes 368, braid 380 and conductors 376 may be arranged concentrically with one another in a coaxially configuration.

Figure 2:
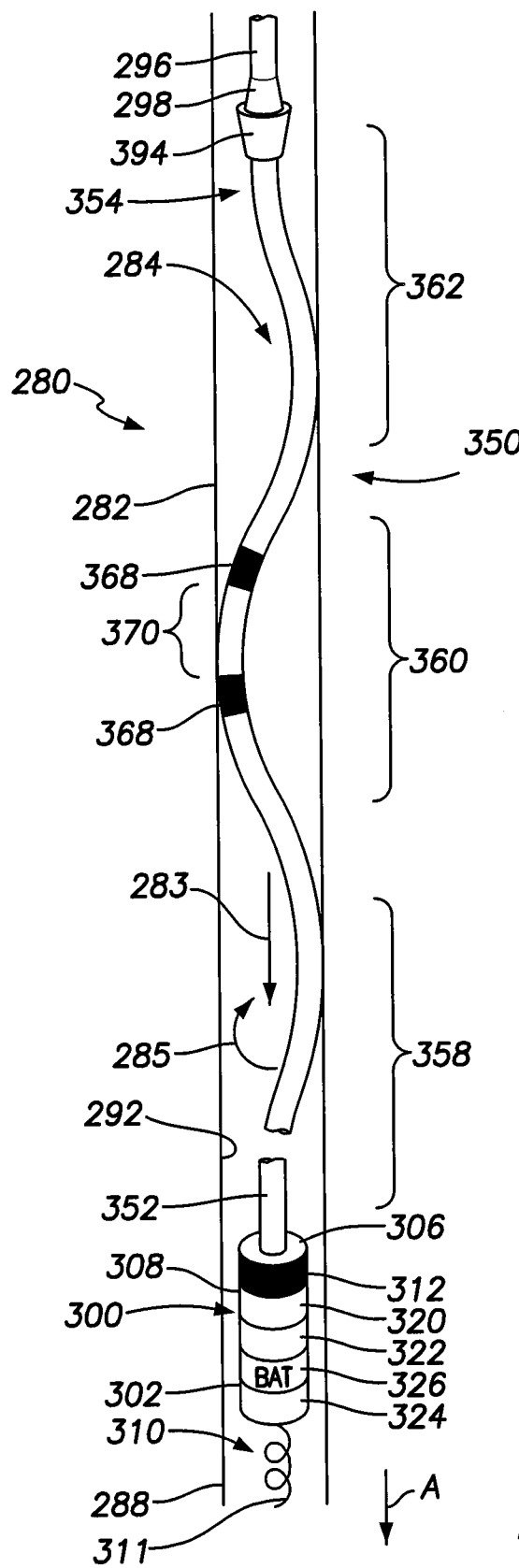
FIG. 2 illustrates a longitudinal axial view of an introducer assembly formed.

FIG. 2 illustrates a longitudinal axial view of an introducer assembly 280, formed according to an embodiment with the LIMD 300 of FIG. 1A inserted therein. The introducer assembly 280 includes a flexible, longitudinal, cylindrical open-ended sheath 282 defining a central internal passage 284. The sheath 282 may be a flexible tube formed of rubber, for example, that is configured to be maneuvered through patient anatomy, such as veins and the heart. In this respect, the sheath 282 may be similar to that of a cardiac catheter.

A physician or surgeon operates user controls on the introducer assembly 280 at a proximal end (not shown). The proximal end may include user controls that allow the sheath 282 to be bent, curved, canted, rotated, twisted, or the like, so as to be navigated through a patient's vasculature. For example, a distal end 288 of the sheath 282 may be bent, curved, canted, rotated, twisted, articulated, or the like through operation by the physician or surgeon manipulating the user controls at the proximal end of the assembly 280.

The LIMD 300 is held in the sheath 282. As shown, the housing 302 of the LIMD 300 slides along inner walls 292 of the sheath 282. The LIMD 300 is configured to be pushed out of, or ejected from, the sheath 282 in the direction of arrow A. The top end 306 of the housing 302 connects to the proximal end 352 of the intra-cardiac extension 350. The extension body 356 extends between the proximal and distal ends 352, 354. The extension body 356 including the chamber transition sub-segment 358, active interim-segment 360 and stabilizer end-segment 362, all of which are "stretched out" or elongated to extend generally along the length of the internal passage 284 of the sheath 282. The extension body 356 is formed of materials that are flexible, yet offer good shape memory such that the extension body 356 may be stretched out while within the sheath 282 and, when removed from the sheath 282, then return to its original (normal, resting) shape as shown in FIG. 1A.

In the example shown in FIG. 2, the active interim-segment 360 is straightened to remove the curved shape only while in the sheath 282. Similarly, the turns 372 of the stabilizer end-segment 362 are straightened. While the example of FIG. 2 illustrates a slight wave or curve that remains in the extension body 356, optionally, the extension body 356 may be constrained to be much straighter or permitted to remain even more curved or bent. The amount to which the active interim-segment 360 and stabilizer end-segment 362 are straightened or curved may vary depending upon the outer dimensions of the extension body 356 and the inner dimensions of the sheath 282.

A pusher rod 296 is provided to be slidably inserted into the sheath 282 in order to manipulate the LIMD 300. For example, the pusher rod 296 may linearly translate the LIMD 300 along the longitudinal axis 283 and rotate the LIMD 300 about the rotational axis 285. The pusher rod 296 includes a pusher tip connector 298 that is configured to securely engage the distal end 354 of the extension body 356. The distal tip 354 includes a connection member 394 that is configured to securely mate with the pusher tip connector 298 (e.g., through a threadable connection, an interference fit, or the like). The pusher rod 296 may extend into and retract from the sheath 282 under a physician's control. The pusher rod 296 and housing 302 are located at opposite ends of the extension body 356. However, rotational force applied by the pusher rod 296 on the distal end 354 of the extension body 356 is substantially all transferred to the housing 302. This rotational force may be used to actively secure the housing 302 to the wall tissue through the active fixation member 310, such as a helical anchor, a coil, a helical wire having a sharp point, a hook, a barb, or the like.

FIG. 2 also illustrates the general internal components of the housing 302. The housing 302 include a charge storage unit 324 and a battery 326 that supplies power to the electronics and energy to the charge storage unit 324. The housing 302 also includes a sensing circuit 322 and a controller 320.

The sensing circuit 322 senses intrinsic activity, while the change storage unit 324 stores high or low energy amounts to be delivered in one or more stimulus pulses. The electrodes 311, 368 may be used to deliver lower energy or high energy stimulus pulses, such as pacing pulses, cardioverter pulse trains, defibrillation shocks and the like. The electrodes 311, 368 may also be used to sense electrical activity, such as physiologic and pathologic behavior and events and provide sensed signals to the sensing circuit 322. The electrodes 311, 312, 368 are configured to be joined to an energy source, such as the charge storage unit 324. The electrodes 311, 368 receive stimulus pulse(s) from the charge storage unit 324. The electrodes 311, 368 may be the same or different size.

The controller 320, within the housing 302, controls the overall functionality of the LIMD 300 including causing the charge storage unit 324 to deliver activation pulses through each of the electrodes 311, 368 in a synchronous manner, based on information from the sensing circuit 322, such that activation pulses delivered from the electrode 368 are timed to initiate activation in the adjacent chamber. The stimulus pulses are delivered synchronously to local and distal activation sites in the local and distal conduction networks such that stimulus pulses delivered at the distal activation site are timed to cause contraction of the adjacent chamber in a predetermined relation to contraction of the local chamber. The electrodes 311, 312, 368 are spaced radially and longitudinally apart from one another such that the local activation site (e.g., right atrium) and the distal activation side in the adjacent chamber (e.g., right ventricle) are sufficiently distant from one another within the heart's conductive network to initiate activation in different branches of the hearts conductive network in a time relation that corresponds to the normal hemodynamic timers (e.g. AV delay).

The controller 320 may operate the LIMD 300 in various modes, such as in select pacemaker modes, select cardiac resynchronization therapy modes, a cardioversion mode, a defibrillation mode and the like. For example, a typical pacing mode may include DDI, DDD, DDO and the like, where the first letter indicates the chamber(s) paced (e.g., A: Atrial pacing; V: Ventricular pacing; and D: Dual-chamber (atrial and ventricular) pacing). The second letter indicates the chamber in which electrical activity is sensed (e.g., A, V, or D). The code O is used when pacemaker discharge is not dependent on sensing electrical activity. The third letter refers to the response to a sensed electric signal (e.g., T: Triggering of pacing function; I: Inhibition of pacing function; D: Dual response (i.e., any spontaneous atrial and ventricular activity will inhibit atrial and ventricular pacing and lone atrial activity will trigger a paced ventricular response) and O: No response to an underlying electric signal (usually related to the absence of associated sensing function)). As examples, the controller 320 may be configured with DDI, DDO, or DDD mode-capable and the LIMD 300 would be placed in the RA, RV, LA or LV.

The sensing circuit 322 receives sensed signals from one or more of the electrodes 311, 368. When pairs of electrodes are provided in the location of electrode 311 or in the location of electrode 368, the sensing circuit 322 discriminates between sensed signals from respective pairs of electrodes that originate in the near field and in the far-field. For example, a pair of electrodes 368 may sense electrical potential across small areas and thereby allow the sensing circuit 322 to discriminate between different sources of electrical signals. In one embodiment, the inter-electrode gap 370 between electrodes 368 is limited or minimized in order to achieve a select type of sensing such as bipolar sensing which limits or minimizes sensing of far-field signals. With a small inter-electrode gap or separation 370, when far-field signals (e.g., signals from the right ventricle, left atrium or left ventricle) reach the electrodes 368 these far-field signals are sensed as a common mode signal with no or a very small potential difference between the electrodes. Similarly, if a pair of electrodes 311 are provided on the active fixation member 310, the electrodes 311 may be separated by a small inter-electrode gap such that, when far-field signals (e.g., signals from the right atrium or left ventricle) reach the electrodes 311 these far-field signals are sensed as a common mode signal with no or a very small potential difference between the electrodes.

As mentioned above, an electrode 312 may be provided on the housing 302 and operate as an anode electrode, while the electrode 311 and/or electrodes 368 may operate as cathode electrodes. When an anode electrode 312 is provided on the housing 302, the controller 320 may be configured to cause stimulus pulses to be delivered between the anode electrode 312 and the first electrode 311 to stimulate the local chamber. When an anode electrode 312 is provided on the housing 302, the sensing circuit 322 may be configured to sense between the anode 312 and the second electrode 368 or between the anode 312 and the first electrode 311.

Figure 3A:
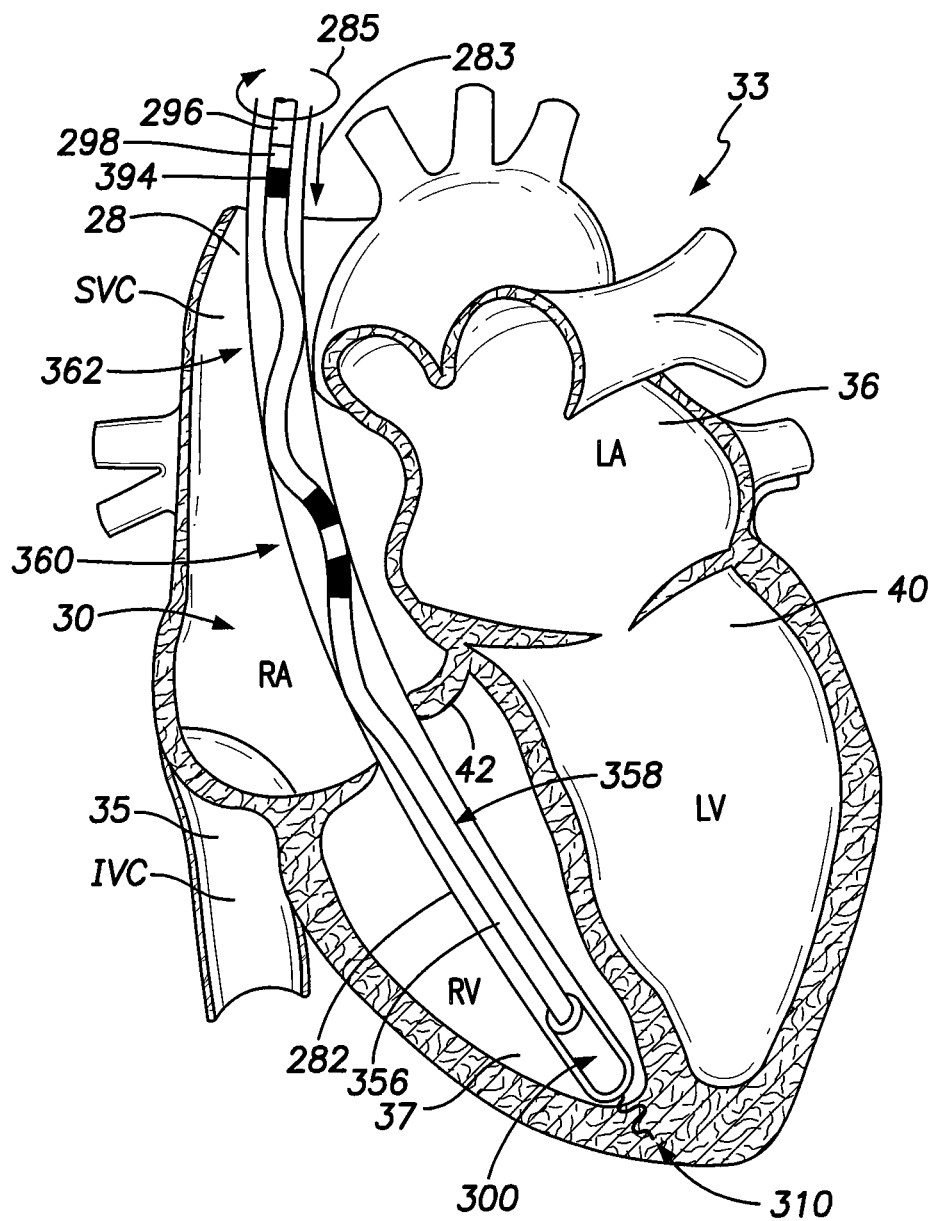
FIGS. 3A and 3B illustrate an exemplary method for delivering the LIMD to desired implantation sites.
Figure 3B:
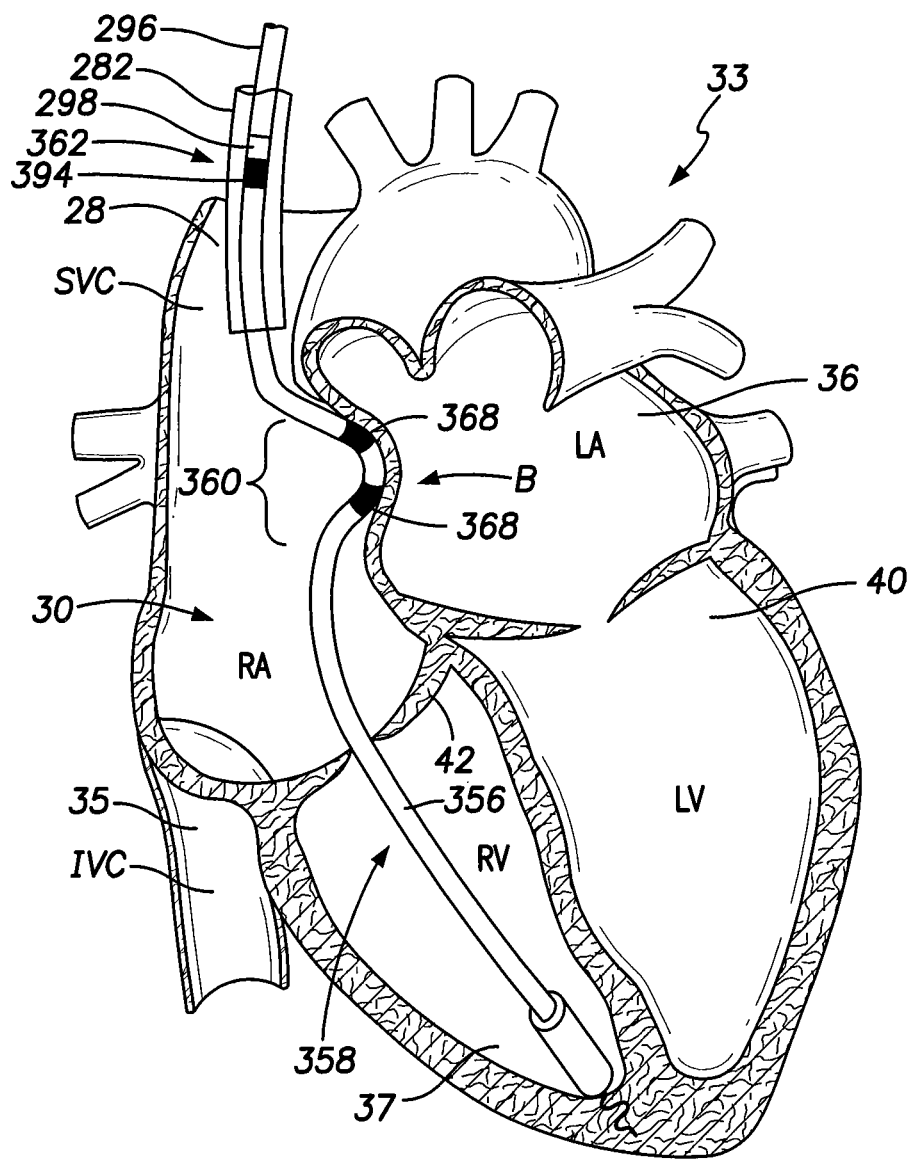

FIGS. 3A and 3B illustrate an exemplary method for delivering the LIMD 300 to desired implantation sites. In the example of FIGS. 3A and 3B, the housing 302 is to be implanted in the RV, while the intra-cardiac extension 350 is to extend from the RV to the RA with an intermediate segment located in the RAA 29 and the distal end located in the SVC. The implantation sheath 282 may represent a sheath used to implant existing leads in the RV. The portions of the intra-cardiac extension 350 located in the SVC and RAA utilize passive fixation mechanisms. This arrangement is designed to prevent premature deployment of the LIMD 300 and to prevent damage to vascular access ways during implantation. The pusher rod 296 may represent any form of pusher implant tool that has a pusher connector tip 298 that affixes to the connection member 394 at the distal end 354 of the intra-cardiac extension 350. The pusher connector tip 298 may use hooks or expanding collets to lock into the connection member 394 at the distal end 354 of the intra-cardiac extension 350.

In step 1, the implantation sheath 282 is steered so that the LIMD 300 is finely navigated to the desired implant site (e.g., RV apex, LV apex, RA, RAA, RA intraventricular septum, LA intraventricular septum, and the like). In the example of FIG. 3A, the sheath 282 is introduced through the RA, through the tricuspid valve, into the RV and extended to the apex of the RV. The sheath 282 and pusher rod 296 navigate the housing 302 to the point where the active fixation member 310 contacts the wall tissue at the RV apex.

Once the desired implantation site in the RV apex is located (via fluoroscopy, echocardiography, or other means), the pusher rod 296 is rotated and longitudinal force is applied, such as in the direction of longitudinal and rotational arrows 283 and 285. The internal framework of the extension body 356 is transversely flexible, with respect to the longitude, but resistant to internal absorption of rotation torque or compression. The braid 380 is one example of an internal framework that affords such characteristics. As the distal end 354 of the intra-cardiac extension 350 is rotated (e.g., clockwise) and downward force is applied, the extension body 356 transfers substantially all of this rotational and longitudinal force to the housing 302 and to the active fixation member 310, thereby causing the active fixation member 310 to rotate in a common direction and by a common degree of rotation as introduced at the pusher rod 296. The rotation causes the active fixation member 310 to engage the helical cathode of the housing 302 into the myocardium of the RV apex, causing it to drill into the tissue.

Once the active fixation member 310 is fully secured in the apex of the RV, optionally, the electrical coupling of the electrode 311 to the RV wall tissue may be verified by ventricular capture and sensing tests. For example, an external device (e.g., programmer or PSA) may communicate wired or wirelessly with the LIMD 300 to instruct the LIMD 300 to deliver stimulus pulse(s) at the electrode 311 and to perform an "auto capture" test to determine whether the stimulus pulse(s) were successful in capturing the RV. The external device may also communicate wired or wirelessly with the LIMD 300 to instruct the LIMD 300 to perform the sensing testing, at electrode 311, and enable sensing electrode(s) to determine whether near field signals (e.g., RA electrical activity) are sensed properly and to determine whether far-field signals (e.g., RV electrical activity) are properly rejected. If the auto-capture and sensing test results are not acceptable, the sheath 282 and pusher rod 296 may be manipulated to navigate the electrode 311 and/or LIMD 300 into a different depth and/or position. Otherwise, if the auto-capture and sensing test results are acceptable, this completes step 1 of the implantation process.

In step 2 of the implantation process, the sheath 282 is partially retracted. In the example of FIGS. 3A and 3B, the sheath 282 is retracted back through the tricuspid valve upward into an upper area of the RA near the SVC. As the sheath 282 is retracted from the RV, the housing 302 and the chamber transition sub-segment 358 of the intra-cardiac extension 350 exit the distal end 288. As the sheath 282 continues to be retracted to a position near the SVC, the active interim-segment 360 exits from the distal end 288. As the chamber transition sub-segment 358 and the active interim-segment 360 exit from the distal end 288, one or both of the chamber transition sub-segment 358 and the active interim-segment 360 change shape from a temporary, extended or dilated introducer state or configuration to a pre-formed, memorized, permanent, implanted state or configuration. The temporary, extended or dilated introducer state or configuration is generally one dimensional, in that it extends substantially along the longitudinal axis of the sheath 282. The pre-formed memorized, permanent, implanted state or configuration is two dimensional or three dimensional, in that it extends along a lateral and/or transverse axis or transverse plane orthogonally to the longitudinal axis of the sheath 282.

Various types of materials may be used to provide the extension body 356 of the intra-cardiac extension 350 with a desired amount of shape memory. For example, the use of the metal braid or mesh core surrounded by silicon, ETFE, OPTIM and the like may be sufficient to afford the desired amount of shape memory.

Optionally, a thermo-responsive shape memory polyurethane (SMPU) may be embedded below and encased within a biocompatible shell (e.g., EFTE). The SMPU represents a smart material that can respond to external heat by changing its macroscopic shape from a temporary configuration to a memorized permanent one. The temporary elongated shape can be maintained while in the sheath 282 which may maintain a certain temperature (the transition temperature). The sheath 282 may maintain the intra-cardiac extension 350 at this temperature until discharged, after which the material of the intra-cardiac extension 350 may change temperature. Thereafter, the material in the intra-cardiac extension 350 will recover its memorized permanent shape.

Upon exiting from the sheath 282, the active interim-segment 360 bends in a curved shape by a distance sufficient to allow elastic protrusion of the passive fixation mechanism 357 into the RAA 29. The steerable sheath 282 is adjusted by the physician until the electrodes 368 in the active interim-segment 360 firmly contact atrial myocardium in the area denoted by arrow B in the RAA tissue 29.

The electrical coupling between the electrodes 368 and wall tissue, following the adjustment step, may be verified by atrial capture and sensing tests. For example, once the active interim-segment 360 is in the desired position, the electrical coupling of the connection may be verified by atrial capture and sensing tests. For example, an external device (e.g., programmer or PSA) may communicate wired or wirelessly with the LIMD 300 to instruct the LIMD 300 to deliver stimulus pulse(s) at the electrodes 368 (or between electrodes 368 and 311) and to perform an "auto capture" test, at the electrodes 368 (or between electrodes 368 and 311), to determine whether the stimulus pulse(s) were successful in capturing the RA. The external device may also communicate wired or wirelessly with the LIMD 300 to instruct the LIMD 300 to perform a sensing operation, at the electrodes 368 (or between electrodes 368 and 312), to determine whether near field intrinsic signals (e.g., RA electrical activity) are being sensing properly and to determine whether far-field signals (e.g., RV electrical activity) are being properly rejected. If the auto-capture and sensing test results are not acceptable, the sheath 282 and pusher rod 296 may be manipulated to navigate the active interim-segment 360 into a different shape and/or position. Otherwise, if the auto-capture and sensing test results are acceptable, this completes step 2 of the implantation process.

In step 3 (the final step), the sheath 282 is fully retracted from the intra-cardiac extension 350 and the pusher connection tip 298 on the pusher rod 296 is disengaged from the connection member 394 at the distal end 354 of the stabilizer end-segment 362. For example, the pusher connection tip 298 may be disengaged from the connection member 394 by unscrewing, releasing an interference connection and the like.

By disconnecting the pusher rod 296, the stabilizer end-segment 362 is enabled to form a coiled shape and to radially expand the diameter of the coiled shape until peripheral edge of the turns 372 engages the SVC (as illustrated in FIG. 1A). This eliminates the SVC-sheath gap illustrated in FIGS. 3A and 3B. With the housing 302 and intra-cardiac extension 350 fully deployed, the overall LIMD 300 is now firmly attached in at least three 3 points of contact with tissue wall. Optionally, the device may attach at two or more than three points.

In alternative embodiments, a stylet (not shown) may also be introduced through the sheath 282 and used to position and form the active interim-segment 360 and stabilizer end-segment 362 into desired SVC coil-shape and/or the RAA J-shape.

Figure 4:
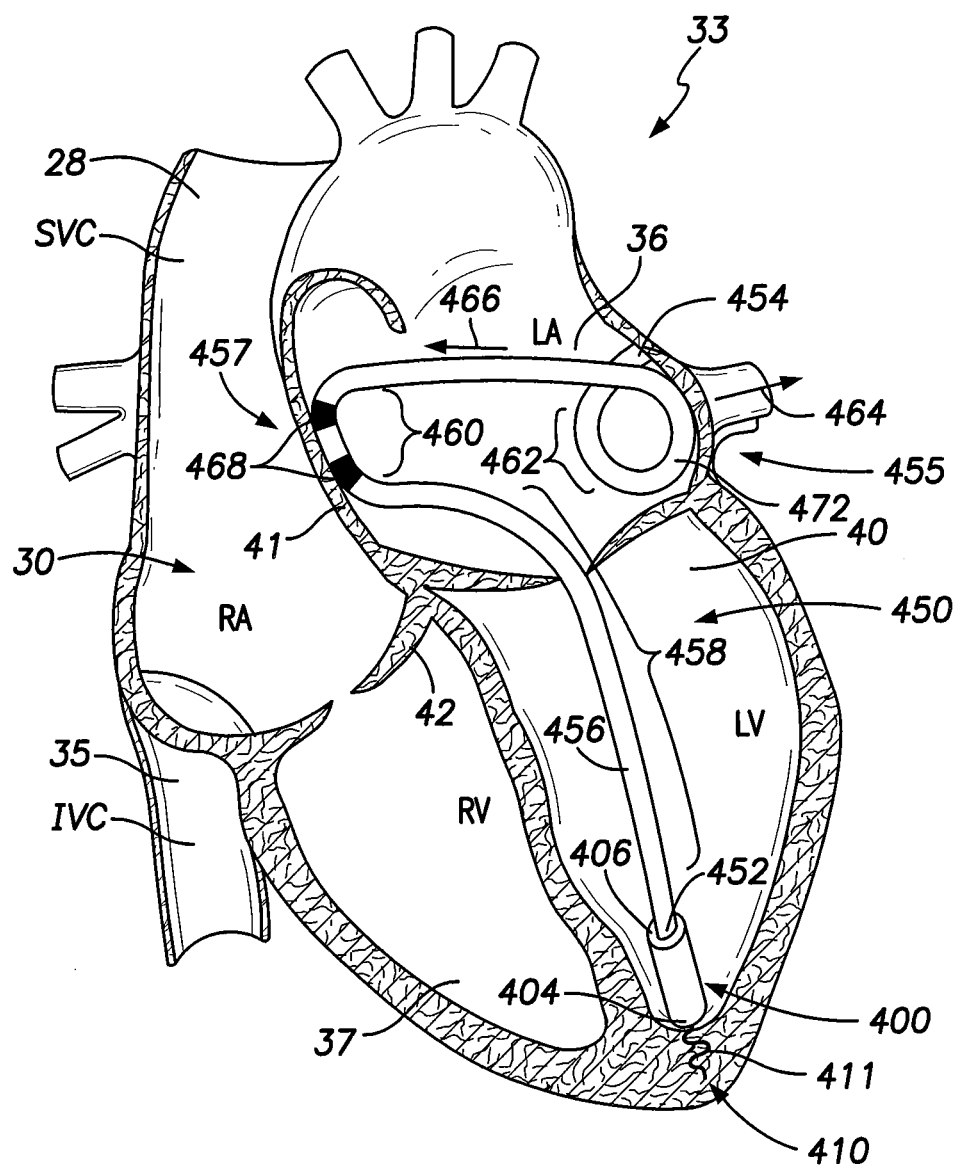
FIG. 4 provides a sectional view of the patient's heart and shows an LIMD implanted in the left side of the heart.

FIG. 4 provides a sectional view of the patient's heart 33 and shows an IMD 400 implanted in the left side of the heart. The IMD 400 has been introduced into the left ventricle through the intraventricular septum, or into the left ventricle through a vein, and the like. The intra-cardiac extension 450 may be inserted through the mitral valve into the left atrium 46. The IMD 400 includes a housing 402 having a base 404 and a top end 406. The housing 402 is elongated and tubular in shape and extends along the longitudinal axis 409. The base 404 is configured to be secured to wall tissue of the left ventricle 40. The base 404 includes an active fixation member 410 provided thereon and extending outward. A first electrode 411 is provided on the active fixation member 410.

The intra-cardiac extension 450 has a proximal end 452, a distal end 454 and a extension body 456 extending there between. The proximal end 452 is permanently or removably coupled to the housing 402 and is located in the left ventricle. The extension body 456 extends between the proximal and distal ends 452 and 454. A stabilization arm, generally denoted at 455, is provided on the distal end 452 of the extension body 456. An appendage fixation mechanism, generally denoted at 457, is provided at an intermediate point along the length of the extension body 456. The extension body 456 including a chamber transition sub-segment 458, an active interim-segment 460 and a stabilizer end-segment 462. The stabilization end-segment 462 is one exemplary structural implementation of the stabilization arm 455. A fixation mechanism 457 is one example of the active interim-segment 460. The chamber transition sub-segment 458 is sufficient in length to extend from the left ventricle to the left atrium.

The stabilizer end-segment 462 is located at the distal end 454 and extending slightly outward in a lateral direction relative to a length of the chamber in which the stabilizer end-segment 462 is located. The stabilizer end-segment 462 engages a first region of the heart. For example, the stabilizer end-segment 462 may extend upward into, and engage, one or more pulmonary veins. The stabilizer end-segment 462 is pre-formed into a predetermined shape based upon which portion of the chamber is to be engaged. The flexible stabilizer end-segment 462 is wrapped into at least one turn 472 with a pre-formed diameter. Optionally, the stabilizer end-segment 462 may utilize alternative shapes, such as an S-shape, a T-shape, a Y-shape, a U-shape and the like. Optionally, the stabilizer end-segment 462 may split into multiple (e.g., 2-4) stabilizer end-segments that project outward and contact different areas of the wall tissue.

The active interim-segment 460 is biased, by the stabilizer end-segment 462, to extend in a second lateral direction 466 away from the direction 464. The active interim-segment 460 has a pre-formed curved shape, such as a large C-shape, or U-shape. The active interim-segment 460 includes electrodes 468 that are provided in a trough area of the C-shape or U-shape. The electrodes 468 are spaced apart from one another, within the trough area. The electrodes 468 are biased in the direction 466 to engage a second region of wall tissue of the adjacent chamber in which the active interim-segment 460 is located.

Figure 5:
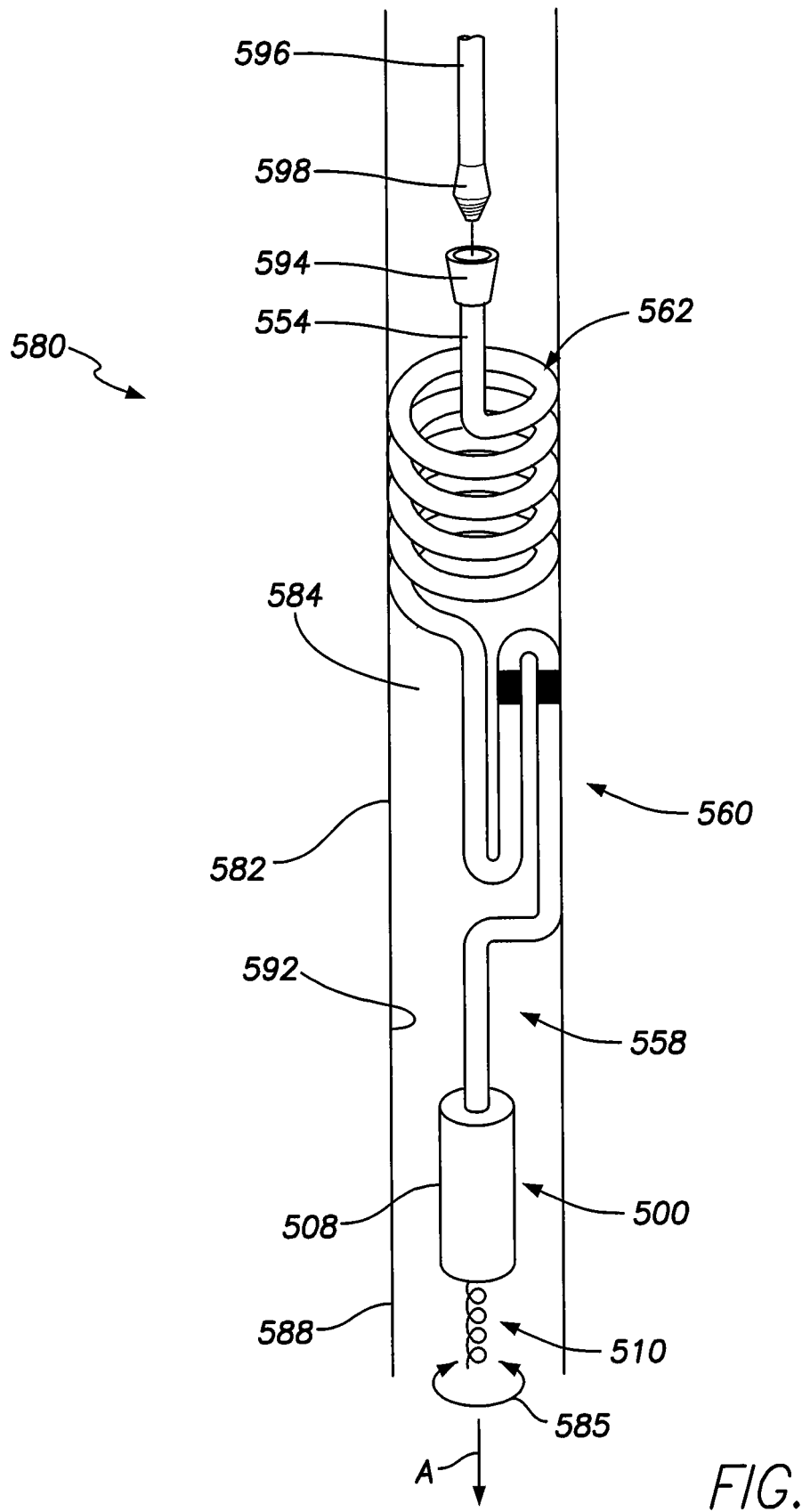
FIG. 5 illustrates a longitudinal axial view of an introducer assembly according to an alternative embodiment with an LIMD inserted therein.

FIG. 5 illustrates a longitudinal axial view of an introducer assembly 580, according to an alternative embodiment with an IMD 500 inserted therein. The introducer assembly 580 includes a flexible, longitudinal, cylindrical open-ended sheath 582 defining a central internal passage 584. A physician or surgeon operates the introducer assembly 580 at a proximal end (not shown). The proximal end may include controls that allow the sheath 582 to be bent, curved, canted, rotated, twisted, or the like, so as to be navigated through a patient's vasculature. In an embodiment, a distal end 588 of the sheath 582 may be bent, curved, canted, rotated, twisted, articulated, or the like through operation by the physician or surgeon who manipulates controls at the proximal end of the assembly 580.

The IMD 500 is located at the distal end 588 of the sheath 582. As shown, the housing 508 of the IMD 500 slides along inner walls 592 of the sheath 582. The IMD 500 is configured to be pushed out of, or ejected from, the sheath 582 in the direction of arrow A. The top end of the IMD 500 connects to the intra-cardiac extension 550. The intra-cardiac extension 550 has a proximal end 552, distal end 554 and extension body 556 extending there between. The extension body 556 including a chamber transition sub-segment 558, an active interim-segment 560 and stabilizer end-segment 562. In the embodiment of FIG. 5, the chamber transition sub-segment 558, active interim-segment 560 and stabilizer end-segment 562 are coiled up and folded over within a shorter region (as compared to the embodiment illustrated in FIG. 2) along the length of the internal passage 584 of the sheath 582. The extension body 556 is formed of materials that are flexible, yet offer good shape memory such that the extension body 556 may be tightly folded onto itself or stretched out while within the sheath 582 and then return to its original (normal, resting) shape as shown in FIGS. 1A and 4.

In the example shown in FIG. 5, the active interim-segment 560 folds over onto itself into a tightly curved shape only while in the sheath 582. The turns 572 of the stabilizer end-segment 562 are more tightly curled (e.g., about a smaller diameter than the diameter of the SVC) than in the deployed state and may be slanted along an acute plane. The amount to which the active interim-segment 560 and stabilizer end-segment 562 are straightened or curved may vary depending upon the outer dimensions of the extension body 556 and the inner dimensions of the sheath 582.

A pusher rod 596 is provided to be slidably inserted into the sheath 582 in order to manipulate the IMD 500. For example, the pusher rod 596 may linearly translate the intra-IMD 500 along the longitudinal axis 583 and rotate the IMD 500 about the rotational axis 585. The pusher rod 596 includes a pusher tip connector 598 that is configured to securely engage the distal end 554 of the extension body 556. The distal tip 554 includes a connection member 594 that is configured to securely mate with the pusher tip connector 598. The pusher rod 596 may extend into and retract from the sheath 582 under a physician's control. The pusher rod 596 and IMD 500 are located at opposite ends of the extension body 550. However, rotational force applied by the pusher rod 596 on the distal end 554 of the extension body 556 is substantially all transferred to the IMD 500. This rotational force may be used to actively secure the IMD 500 to the wall tissue through an active fixation member 510, such as a helical anchor, a coil, a helical wire having a sharp point, a hook, a barb, or the like, that is configured to secure the IMD 500 into tissue of the heart wall.

Figure 6:
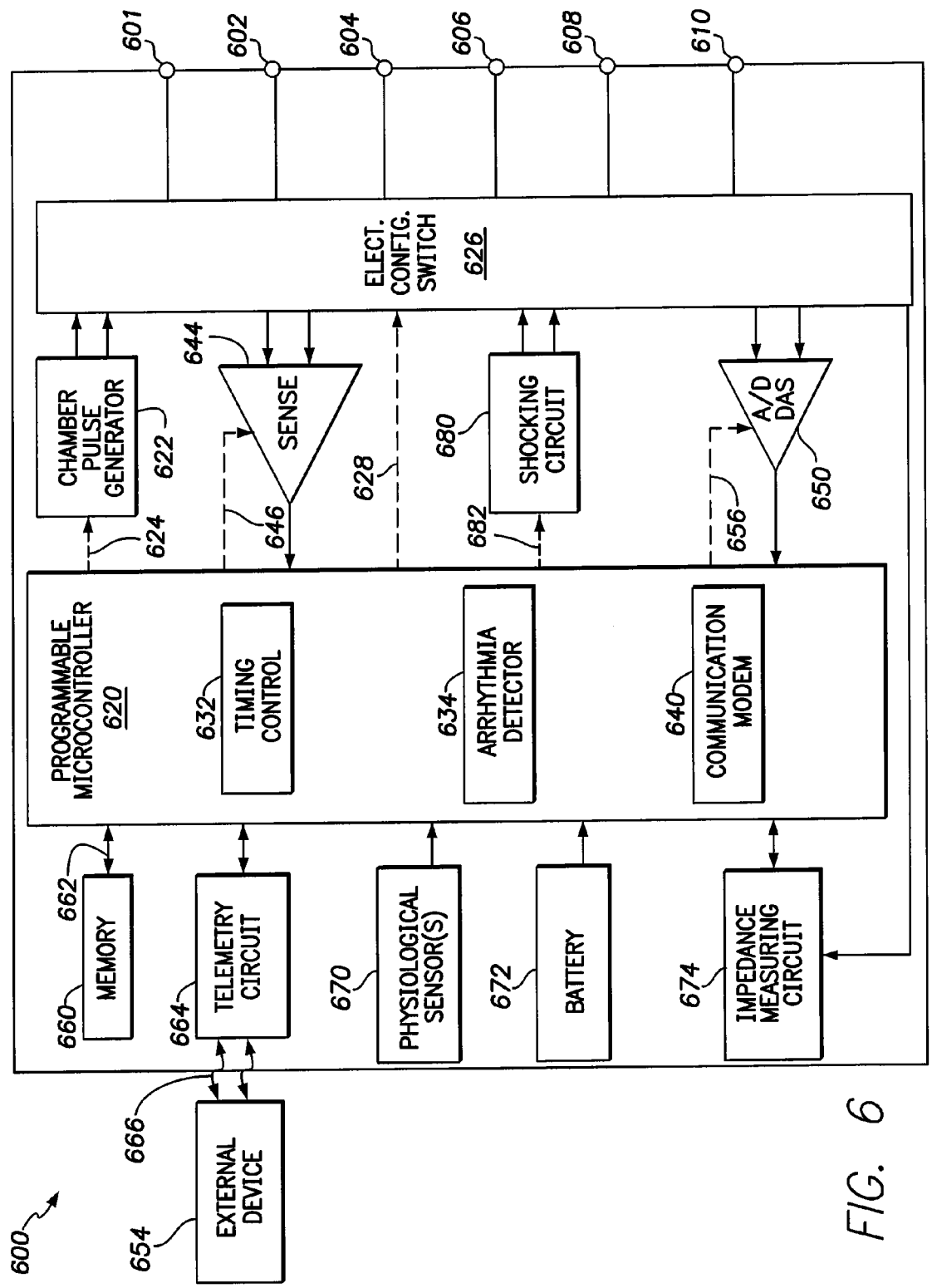
FIG. 6 illustrates an exemplary block diagram of the electrical components of the housing of the LIMD of FIGS. 1-5.

FIG. 6 is a block diagram of an exemplary LIMD 600 configured for dual-chamber functionality from a primary location within a single side of the heart. For example, the LIMD 600 may be implemented as a full-function biventricular pacemaker, equipped with both atrial and ventricular sensing and pacing circuitry for four chamber sensing and stimulation therapy (including both pacing and shock treatment). Alternatively, the LIMD may be implemented with a reduced set of functions and components. For instance, the LIMD may be implemented without impedance measuring circuitry.

The LIMD 600 has a housing 601 to hold the electronic/computing components. The housing 601 (which is often referred to as the "can", "case", "encasing", or "case electrode") may be programmably selected to act as the return electrode for certain stimulus modes. Housing 601 further includes a plurality of terminals 602, 604, 606, 608, 610 that interface with electrodes of the LIMD. For example, the terminals may include a terminal 602 that connects with a first electrode associated with the housing (e.g. tip electrode 311) and located in a first chamber; a terminal 604 that connects with a second electrode associated with the housing (e.g., ring electrode 312) and also located in the first chamber; a terminal 606 that connects with a third electrode associated with the intra-cardiac extension (e.g. ring electrode 368) and located in the second chamber; a terminal 608 that connects with a fourth electrode associated with the intra-cardiac extension and also located in the second chamber; and an additional terminals 610 that connect with one or more additional electrodes, if available. The type and location of each electrode may vary. For example, the electrodes may include various combinations of ring, tip, coil and shocking electrodes and the like.

The housing 602 includes a programmable microcontroller 620 that controls various operations of the LIMD, including cardiac monitoring and stimulation therapy. Microcontroller 620 includes a microprocessor (or equivalent control circuitry), RAM and/or ROM memory, logic and timing circuitry, state machine circuitry, and I/O circuitry.

Housing 601 further includes a first chamber pulse generator 622 that generates stimulation pulses for delivery by one or more electrodes coupled thereto. The pulse generator 622 is controlled by the microcontroller 620 via control signal 624. The pulse generator 622 is coupled to the select electrode(s) via an electrode configuration switch 626, which includes multiple switches for connecting the desired electrodes to the appropriate I/O circuits, thereby facilitating electrode programmability. The switch 626 is controlled by a control signal 628 from the microcontroller 620.

In the example of FIG. 6, a single pulse generator 622 is illustrated. Optionally, the housing 601 may include multiple pulse generators, similar to pulse generator 622, where each pulse generator is coupled to one or more electrodes and controlled by the microcontroller 620 to deliver select stimulus pulse(s) to the corresponding one or more electrodes.

Microcontroller 620 is illustrated as including timing control circuitry 632 to control the timing of the stimulation pulses (e.g., pacing rate, atrio-ventricular (AV) delay, atrial interconduction (A-A) delay, or ventricular interconduction (V-V) delay, etc.). The timing control circuitry 632 may also be used for the timing of refractory periods, blanking intervals, noise detection windows, evoked response windows, alert intervals, marker channel timing, and so on. Microcontroller 620 also has an arrhythmia detector 634 for detecting arrhythmia conditions and a morphology detector 636. Although not shown, the microcontroller 620 may further include other dedicated circuitry and/or firmware/software components that assist in monitoring various conditions of the patient's heart and managing pacing therapies.

The housing 601 includes sensing circuitry 644 selectively coupled to one or more electrodes that perform sensing operations, through the switch 626 to detect the presence of cardiac activity in the corresponding chambers of the heart. The sensing circuit 644 is configured to perform bipolar sensing between one pair of electrodes and/or between multiple pairs of electrodes. The sensing circuit 644 detects near-field electrical activity and rejects far-field electrical activity. The sensing circuitry 644 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 626 determines the sensing polarity of the cardiac signal by selectively closing the appropriate switches. In this way, the clinician may program the sensing polarity independent of the stimulation polarity.

The output of the sensing circuitry 644 is connected to the microcontroller 620 which, in turn, triggers or inhibits the pulse generator 622 in response to the absence or presence of cardiac activity. The sensing circuitry 644 receives a control signal 646 from the microcontroller 620 for purposes of controlling the gain, threshold, polarization charge removal circuitry (not shown), and the timing of any blocking circuitry (not shown) coupled to the inputs of the sensing circuitry.

In the example of FIG. 6, a single sensing circuit 644 is illustrated. Optionally, the IMD 602 may include multiple sensing circuit, similar to sensing circuit 644, where each sensing circuit is coupled to one or more electrodes and controlled by the microcontroller 620 to sense electrical activity detected at the corresponding one or more electrodes. The sensing circuit 644 may operate in a unipolar sensing configuration or in a bipolar sensing configuration.

The housing 601 further includes an analog-to-digital (A/D) data acquisition system (DAS) 650 coupled to one or more electrodes via the switch 626 to sample cardiac signals across any pair of desired electrodes. The data acquisition system 650 is configured to acquire intracardiac electrogram signals, convert the raw analog data into digital data, and store the digital data for later processing and/or telemetric transmission to an external device 654 (e.g., a programmer, local transceiver, or a diagnostic system analyzer). The data acquisition system 650 is controlled by a control signal 656 from the microcontroller 620.

The microcontroller 620 is coupled to a memory 660 by a suitable data/address bus 662. The programmable operating parameters used by the microcontroller 620 are stored in memory 660 and used to customize the operation of the LIMD 600 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the LIMD 600 may be non-invasively programmed into the memory 660 through a telemetry circuit 664 in telemetric communication via communication link 666 with the external device 654. The telemetry circuit 664 allows intracardiac electrograms and status information relating to the operation of the LIMD 600 (as contained in the microcontroller 620 or memory 660) to be sent to the external device 654 through the established communication link 666.

The housing 601 can further include magnet detection circuitry (not shown), coupled to the microcontroller 620, to detect when a magnet is placed over the unit. A magnet may be used by a clinician to perform various test functions of the unit 602 and/or to signal the microcontroller 620 that the external programmer 654 is in place to receive or transmit data to the microcontroller 620 through the telemetry circuits 664.

The LIMD 600 may be equipped with a communication modem (modulator/demodulator) 640 to enable wireless communication with a remote device, such as a second implanted LIMD in a master/slave arrangement, such as described in U.S. Pat. No. 7,630,767. In one implementation, the communication modem 640 uses high frequency modulation. As one example, the modem 640 transmits signals between a pair of LIMD electrodes, such as between the can defining the housing 601 and anyone of the electrodes connected to terminals 602-610. The signals are transmitted in a high frequency range of approximately 20-80 kHz, as such signals travel through the body tissue in fluids without stimulating the heart or being felt by the patient. The communication modem 640 may be implemented in hardware as part of the microcontroller 620, or as software/firmware instructions programmed into and executed by the microcontroller 620. Alternatively, the modem 640 may reside separately from the microcontroller as a standalone component.

The housing 600 can further include one or more physiologic sensors 670. Such sensors are commonly referred to as "rate-responsive" sensors because they are typically used to adjust pacing stimulation rates according to the exercise state of the patient. However, the physiological sensor 670 may further be used to detect changes in cardiac output, changes in the physiological condition of the heart, or diurnal changes in activity (e.g., detecting sleep and wake states). Signals generated by the physiological sensors 670 are passed to the microcontroller 620 for analysis. The microcontroller 620 responds by adjusting the various pacing parameters (such as rate, AV Delay, V-V Delay, etc.) at which the atrial and ventricular pacing pulses are administered. While shown as being included within the unit 602, the physiologic sensor(s) 670 may be external to the unit 602, yet still be implanted within or carried by the patient. Examples of physiologic sensors might include sensors that, for example, sense respiration rate, pH of blood, ventricular gradient, activity, position/posture, minute ventilation (MV), and so forth.

A battery 672 provides operating power to all components of the housing 600. The battery 672 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 672 also desirably has a predictable discharge characteristic so that elective replacement time can be detected. As one example, the unit 602 employs lithium/silver vanadium oxide batteries.

The housing 600 may further include an impedance measuring circuit 674, which can be used for many things, including: extension impedance surveillance during the acute and chronic phases for proper extension positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 674 is coupled to the switch 626 so that any desired electrode may be used. The microcontroller 620 may further controls a shocking circuit 680 by way of a control signal 682. The shocking circuit 680 generates shocking pulses of low (e.g., up to 0.5 joules), moderate (e.g., 0.5-10 joules), or high energy (e.g., 611 to 40 joules), as controlled by the microcontroller 620.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A leadless intra-cardiac medical device (LIMD), comprising:
a housing configured to be implanted entirely within a single local chamber of the heart;
a base on the housing, the base configured to be secured to the local chamber;
a first electrode provided on the housing at a first position such that, when the housing is implanted in the local chamber, the first electrode is configured to engage wall tissue at a local activation site within a conduction network of the local chamber;
an intra-cardiac extension having a proximal end, a distal end and an extension body extending there between, the proximal end coupled to the housing and located in the local chamber, the extension body including a stabilization arm provided at the distal end thereof, the extension body being sufficient in length to extend from the local chamber into an adjacent chamber, the extension body including an active interim-segment located at an intermediate point along the extension body;
wherein the stabilization arm includes a stabilizer end-segment located at the distal end and extending in a first lateral direction to engage a first region of the heart, the active interim-segment extending in a second lateral direction to engage a second region of wall tissue of the adjacent chamber;
a second electrode provided on the active interim-segment of the extension body, the second electrode configured to engage wall tissue at a distal activation site within a conduction network of the adjacent chamber; and
a controller, within the housing, configured to cause stimulus pulses to be delivered, in a dual chamber synchronous manner, through the first and second electrodes to the local and distal activation sites, respectively.

2. The device of claim 1, wherein the controller is configured to control delivery of the stimulus pulses from the first and second electrodes in accordance with a DDD pacing mode to a right atrium and right ventricle, while the housing is entirely located in one of the right atrium and right ventricle.

3. The device of claim 1, wherein the controller is configured to control delivery of the stimulus pulses from the first and second electrodes in accordance with a DDD pacing mode to a left atrium and left ventricle, while the housing is entirely located in one of the left atrium and left ventricle.

4. The device of claim 1, wherein the active interim-segment is located between the stabilization arm and the proximal end, the active interim-segment and the stabilization arm extend into and engage opposed areas of the local wall tissue of the local chamber.

5. The device of claim 1, wherein the extension body is comprised of a flexible material having a pre-formed, memorized, permanent implanted state that is shaped to conform to select anatomical contours in the heart and to bias the active interim-segment and stabilization arm against the wall tissue at regions of interest.

6. The device of claim 1, further comprising an anode electrode on the housing, the controller configured to cause stimulus pulses to be delivered between the anode electrode and the first electrode to stimulate the local chamber.

7. The device of claim 1, further comprising an anode electrode on the housing, and a sensing circuit configured to sense between the anode and the second electrode.

8. The device of claim 1, further comprising a third electrode, the second and third electrodes located on the active interim-segment, the second and third electrodes being electrically separated from one another and configured to operate in at least one of a bipolar sensing mode and a bipolar pacing mode.

9. A leadless intra-cardiac medical device (LIMD), comprising:
a housing configured to be implanted entirely within a single local chamber of the heart;
a base on the housing, the base configured to be secured to the local chamber;
a first electrode provided on the housing at a first position such that, when the housing is implanted in the local chamber, the first electrode is configured to engage wall tissue at a local activation site within a conduction network of the local chamber;
an intra-cardiac extension having a proximal end, a distal end and an extension body extending there between, the proximal end coupled to the housing and located in the local chamber, the extension body including a stabilization arm provided at the distal end thereof, the extension body being sufficient in length to extend from the local chamber into an adjacent chamber, the extension body including an active interim-segment located at an intermediate point along the extension body;
a second electrode provided on the active interim-segment of the extension body, the second electrode configured to engage wall tissue at a distal activation site within a conduction network of the adjacent chamber; and
a controller, within the housing, configured to cause stimulus pulses to be delivered, in a dual chamber synchronous manner, through the first and second electrodes to the local and distal activation sites, respectively;
wherein the active interim-segment is pre-formed in a curved shape having a trough, the second electrode and a third electrode located on the extension body in the trough, the curved shape configured to following a contour of an interior of a right atrial appendage.

10. The device of claim 9, wherein the first and second regions represent a superior vena cava and a right atrial appendage of the right atrium, respectively.

11. A leadless intra-cardiac medical device (LIMD), comprising:
a housing configured to be implanted entirely within a single local chamber of the heart;
a base on the housing, the base configured to be secured to the local chamber;
a first electrode provided on the housing at a first position such that, when the housing is implanted in the local chamber, the first electrode is configured to engage wall tissue at a local activation site within a conduction network of the local chamber;
an intra-cardiac extension having a proximal end, a distal end and an extension body extending there between, the proximal end coupled to the housing and located in the local chamber, the extension body including a stabilization arm provided at the distal end thereof, the extension body being sufficient in length to extend from the local chamber into an adjacent chamber, the extension body including an active interim-segment located at an intermediate point along the extension body;
a second electrode provided on the active interim-segment of the extension body, the second electrode configured to engage wall tissue at a distal activation site within a conduction network of the adjacent chamber; and
a controller, within the housing, configured to cause stimulus pulses to be delivered, in a dual chamber synchronous manner, through the first and second electrodes to the local and distal activation sites, respectively;

wherein the controller is configured to time delivery of the stimulus pulses at the distal activation site to cause contraction of the adjacent chamber in a predetermined relation to contraction of the local chamber.

12. A leadless intra-cardiac medical device (LIMD), comprising:
a housing configured to be implanted entirely within a single local chamber of the heart;
a base on the housing, the base configured to be secured to the local chamber;
a first electrode provided on the housing at a first position such that, when the housing is implanted in the local chamber, the first electrode is configured to engage wall tissue at a local activation site within a conduction network of the local chamber;
an intra-cardiac extension having a proximal end, a distal end and an extension body extending there between, the proximal end coupled to the housing and located in the local chamber, the extension body including a stabilization arm provided at the distal end thereof, the extension body being sufficient in length to extend from the local chamber into an adjacent chamber, the extension body including an active interim-segment located at an intermediate point along the extension body;
a second electrode provided on the active interim-segment of the extension body, the second electrode configured to engage wall tissue at a distal activation site within a conduction network of the adjacent chamber; and
a controller, within the housing, configured to cause stimulus pulses to be delivered, in a dual chamber synchronous manner, through the first and second electrodes to the local and distal activation sites, respectively;
wherein the stabilization arm includes a flexible stabilizer end-segment wrapped into at least one turn.

13. A leadless intra-cardiac medical device (LIMD), comprising:
a housing configured to be implanted entirely within a single local chamber of the heart:
a base on the housing, the base configured to be secured to the local chamber;
a first electrode provided on the housing at a first position such that, when the housing is implanted in the local chamber, the first electrode is configured to engage wall tissue at a local activation site within a conduction network of the local chamber;
an intra-cardiac extension having a proximal end, a distal end and an extension body extending there between, the proximal end coupled to the housing and located in the local chamber, the extension body including a stabilization arm provided at the distal end thereof, the extension body being sufficient in length to extend from the local chamber into an adjacent chamber, the extension body including an active interim-segment located at an intermediate point along the extension body;
a second electrode provided on the active interim-segment of the extension body, the second electrode configured to engage wall tissue at a distal activation site within a conduction network of the adjacent chamber; and
a controller, within the housing, configured to cause stimulus pulses to be delivered, in a dual chamber synchronous manner, through the first and second electrodes to the local and distal activation sites, respectively; and
further comprising a conductor wire extending within the extension body from the housing to the second electrode, the conductor terminating at the second electrode, the stabilization arm being void of electrodes and conductor wires.

14. A method for implanting a leadless intra-cardiac medical device (LIMD), the LIMD including a housing with a base, a first electrode provided on the housing, an intra-cardiac extension having a proximal end, a distal end and an extension body extending there between, the proximal end coupled to the, the extension body including a stabilization extension provided at the distal end of the intra-cardiac extension, and an active interim-segment located at an intermediate point along the extension body between the stabilization extension and the proximal end of the intra-cardiac extension, a second electrode provided on the active interim-segment, the method comprising:
guiding the housing, utilizing an introducer, to a local activation site within a conductive network of the local chamber;
positioning the first electrode to engage wall tissue at the local activation site within the conductive network of the local chamber;
actively securing the housing to tissue of interest at the local activation site by applying rotational force to the stabilization extension which causes an active fixation member on the housing to become securely affixed to the wall tissue;
guiding the active interim-segment, utilizing the introducer, to a distal activation site within a conductive network of an adjacent chamber;
positioning the second electrode to engage tissue of interest at the distal activation site within the conductive network of the adjacent chamber; and
configuring a controller within the housing to cause stimulus pulses to be delivered, in a dual chamber synchronous manner, through the first electrode to the local activation site, and through the second electrode to the distal activation site.

15. The method of claim 14, wherein the active interim-segment further comprises a third electrode electrically separated from the second electrode, the method further comprising configuring the controller to operate in at least one of a bipolar sensing mode and a bipolar pacing mode using the second and third electrodes.

16. The method of claim 15, wherein the active interim-segment is pre-formed in a curved shape having a trough, the second and third electrodes located in the trough, the curved shape configured to following a contour of an interior of a right atrial appendage.

17. The method of claim 14, further comprising:
loading the IMD into a sheath of the introducer such that a memorized, pre-formed shape of the intra-cardiac extension is changed to a temporary, extended or dilated introducer state; and
after securing the housing to the tissue of interest, at least partially retracting the introducer such that, as the intra-cardiac extension is discharged from a distal end of the sheath, thereby allowing the intra-cardiac extension to return to the memorized, pre-formed shape.

18. The method of claim 14, further comprising performing an auto capture test to determine whether stimulus pulses delivered from the first electrode at the local activation site capture the local chamber.

19. The method of claim 14, further comprising performing a sensing test to determine whether far-field signals sensed at least partially by the first electrode are rejected as far-field signals.

20. The method of claim 14, further comprising, when the active interim-segment exits from the introducer, permitting the active interim-segment to bend into a curved shape sufficient to extend into and engage a contour of an interior of the heart or vessel.

21. The method of claim 14, further comprising guiding the stabilization extension to engage a first region of the heart, the first region representing at least one of a superior vena cava, an inferior vena cava, a coronary sinus, and a pulmonary artery.

22. The method of claim 14, wherein the stabilization arm includes a stabilizer end-segment that is pre-formed to wrap into at least one turn that is predisposed to radially expand to a diameter sufficient to fit against an interior of at least one of a superior vena cava, an inferior vena cava, a coronary sinus, and a pulmonary artery.

23. The method of claim 14, further comprising configuring the controller to control delivery of the stimulus pulses from the first and second electrodes in accordance with a DDD pacing mode to a right atrium and right ventricle, while the housing is entirely located in right side of the heart.

24. The method of claim 14, further comprising configuring the controller to control delivery of the stimulus pulses from the first and second electrodes in accordance with a DDD pacing mode to a left atrium and left ventricle, while the housing is entirely located in left side of the heart.

* * * * *